(12) United States Patent
Boomgaarden et al.

(10) Patent No.: US 7,497,625 B2
(45) Date of Patent: Mar. 3, 2009

(54) SYSTEMS, METHODS AND APPARATUS OF AN EXTENDING COLUMN

(75) Inventors: Jonathon Carl Boomgaarden, Waukesha, WI (US); Philip Olikara, Brookfield, WI (US)

(73) Assignee: General Electric Company, Schenectady, NY (US)

(*) Notice: Subject to any disclaimer, the term of this patent is extended or adjusted under 35 U.S.C. 154(b) by 333 days.

(21) Appl. No.: 10/863,993

(22) Filed: Jun. 8, 2004

(65) Prior Publication Data

US 2005/0281388 A1 Dec. 22, 2005

(51) Int. Cl.
*F16C 17/00* (2006.01)
*H05G 1/02* (2006.01)

(52) U.S. Cl. .......................... 384/7; 378/197

(58) Field of Classification Search ............ 384/7, 384/38–45, 48, 57, 100; 378/34, 81–85, 378/193–199, 299; 414/294, 401, 663
See application file for complete search history.

(56) References Cited

U.S. PATENT DOCUMENTS

| | | | | | |
|---|---|---|---|---|---|
| 3,155,383 | A | * | 11/1964 | Whitmore | 384/100 |
| 4,021,715 | A | | 5/1977 | Von Hacht et al. | |
| 4,630,872 | A | * | 12/1986 | Teramachi | 384/45 |
| 4,671,728 | A | * | 6/1987 | Clark et al. | 414/401 |
| H313 | H | * | 7/1987 | Staudenmann et al. | 378/81 |
| 4,769,565 | A | * | 9/1988 | Teramachi | 384/45 |
| 5,048,069 | A | * | 9/1991 | Siczek | 378/197 |
| 5,050,202 | A | | 9/1991 | Yanome | |
| 5,157,707 | A | | 10/1992 | Ohlson | |
| 5,388,913 | A | * | 2/1995 | Cawley | 384/38 |
| 5,506,879 | A | * | 4/1996 | Mori et al. | 378/39 |
| 5,636,259 | A | | 6/1997 | Khutoryansky et al. | |
| 5,658,078 | A | * | 8/1997 | Cawley | 384/7 |
| 5,671,266 | A | | 9/1997 | Linhart | |
| 5,751,788 | A | | 5/1998 | Khutoryansky et al. | |
| 5,768,336 | A | | 6/1998 | Khutoryansky et al. | |
| 5,870,450 | A | | 2/1999 | Khutoryansky et al. | |
| 5,917,882 | A | | 6/1999 | Khutoryansky et al. | |
| 6,128,006 | A | | 10/2000 | Rosenberg et al. | |
| 6,155,716 | A | * | 12/2000 | Okamura et al. | 384/7 |
| 6,240,582 | B1 | * | 6/2001 | Reinke | 378/209 |
| 6,282,264 | B1 | | 8/2001 | Smith et al. | |
| 6,459,226 | B1 | | 10/2002 | Zettel et al. | |
| 6,552,449 | B2 | * | 4/2003 | Tsuboi et al. | 378/34 |
| 6,857,147 | B2 | | 2/2005 | Somasundaram | |
| 6,952,180 | B2 | | 10/2005 | Jonsson et al. | |
| 6,986,179 | B2 | | 1/2006 | Varadharajulu et al. | |
| 7,177,393 | B2 | | 7/2007 | Kanemitsu | |
| 2002/0112016 | A1 | | 8/2002 | Peshkin et al. | |
| 2003/0095635 | A1 | * | 5/2003 | Moritake et al. | 378/198 |
| 2004/0131159 | A1 | * | 7/2004 | McKenna | 378/209 |

FOREIGN PATENT DOCUMENTS

WO 2004049946 A1 6/2004

* cited by examiner

*Primary Examiner*—Marcus Charles
(74) *Attorney, Agent, or Firm*—Peter Vogel, Esq.; Bill Baxter, Esq.; Michael G. Smith, Esq.

(57) ABSTRACT

Systems, methods and apparatus are provided through which, in some embodiments, an extending column is comprised of a plurality of stacked slides that are mounted to each other through linear bearing assemblies that allow the extending column to telescope inward and outward. Some embodiments of the extending column have a synchronization mechanism between each slide to extend each slide in equal distances relative to each other.

30 Claims, 11 Drawing Sheets

SYSTEMS, METHODS AND APPARATUS OF AN EXTENDING COLUMN

FIELD OF THE INVENTION

This invention relates generally to equipment extending columns, and more particularly to X-ray tube and collimator extending columns.

BACKGROUND OF THE INVENTION

In conventional medical diagnostic X-ray radiography, an X-ray source and a collimator are suspended from a ceiling by an extending column. The extending column is often referred to as an overhead tube suspension system. The X-ray source sends a beam of X-rays from the X-ray source behind the patient, through the patient's chest, to the recording medium (e.g. film or digital recording means). A collimator is a diaphragm or system of diaphragms made of an absorbing material, designed to define and restrict the dimensions and direction of a beam of radiation from the X-ray source.

The extending column is mounted to carriages to provide freedom of motion that allows general positioning of the X-ray source at the desired location and orientation within an X-ray examination room. In conventional extending columns, the extending column consists of a series of concentric cylinders, either circular or prismatic (e.g. octagonal), with ball bearing assemblies running in channels or on tracks in at least two planes to provide smooth motion with as little free play as possible. In one embodiment, the ball bearing assemblies are on opposing sides of the concentric cylinder. The amount of free play in the extending column is minimized by closely controlling tolerances, and also by providing adjustment means to reduce the clearance for the bearings as much as possible. Conventional extending columns are approximately symmetrical, with guiding and synchronizing means being distributed approximately equally in 2, 3, or 4 sides of the columns.

One problem with conventional extending columns is that the precision of motion is poor, since it is very difficult to manufacture the telescoping sections precisely enough to maintain the parallelism and straightness required among the various column sections thus employed.

Another problem is that that adjustment of the bearings is difficult, and this leads to inconsistencies in moving efforts and stiffness, as well as lost motion in the assemblies.

Yet another problem is that synchronized motion of the column sections is achieved through the use of "J-bars" and the like, which are long bars extending from one section into the next. These J-bars often rub against the sections, which increases friction in movement, which in turn increases wear of the extending column and requires a greater manual force by an operator of the X-ray equipment to position the X-ray source and the collimator mounted on the extending column.

Still yet another problem is that the length of travel permissible for a given column length is limited, because the bearings are not stiff enough if spaced close together. As a result, clinical usage is somewhat restricted, and extensions are sometimes employed to achieve the desired anatomical coverage range.

A further problem is the size of the conventional extending columns. The area close to an X-ray examination table has rather close quarters for the operators of the X-ray equipment. Reducing the size of the extending column would provide more room for the operators.

For the reasons stated above, and for other reasons stated below which will become apparent to those skilled in the art upon reading and understanding the present specification, there is a need in the art for an extending column for medical diagnostic that has improved precision of motion. There is also a need for reducing inconsistencies in moving efforts and stiffness, as well as reducing lost motion in the assemblies. There is an additional need to reduce the rubbing of J-bars against sections. There is a further need increase rigidity in order to improve clinical usage without the need for extensions to achieve the desired anatomical coverage range. There is also a need to reduce the size of the extending column.

BRIEF DESCRIPTION OF THE INVENTION

The above-mentioned shortcomings, disadvantages and problems are addressed herein, which will be understood by reading and studying the following specification.

In one aspect, and improved means for providing the extension motion for the column by an extending column that includes a plurality of stacked slides that are mounted to each other through linear bearing assemblies that allow the extending column to telescope inward and outward. Some embodiments of the extending column have a synchronization mechanism between each slide to extend each slide in equal distances relative to each other.

In one aspect, an asymmetrical apparatus includes an outer section that is mountable to a supporting structure for the apparatus, a first linear bearing assembly coupled to the outer section, a first moveable linear slide base that is operably coupled to first linear bearing assembly, a second linear bearing assembly that is operably coupled to the first moveable linear slide base, and a second moveable linear slide base that is operably coupled to the second linear bearing assembly.

In another aspect, an apparatus includes an outer section, mountable to a supporting structure for the apparatus, a plurality of linear slide bases, a first linear slide base of the plurality of linear slide bases being mounted on the outer section, the plurality of linear slide bases being constrained to move in a rectilinear motion with respect to each other by linear bearings, and at least one medical diagnostic apparatus mounted on the last of the plurality of linear slide bases.

In yet another aspect, a system includes an outer section that is mountable to a supporting structure for the system, and a plurality of concave linear slide bases in which a first linear slide base of the plurality of linear slide bases being mounted on the outer section, each concave linear slide bases is successively smaller than an immediately previous concave linear slide bases to the extent that each concave linear slide bases fits into the immediately previous concave linear slide base and the plurality of linear slide bases are constrained to move in a rectilinear motion with respect to each other by linear bearings.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of embodiments are described. In the third section, a conclusion of the detailed description is provided.

System Level Overviews

Figure 1:
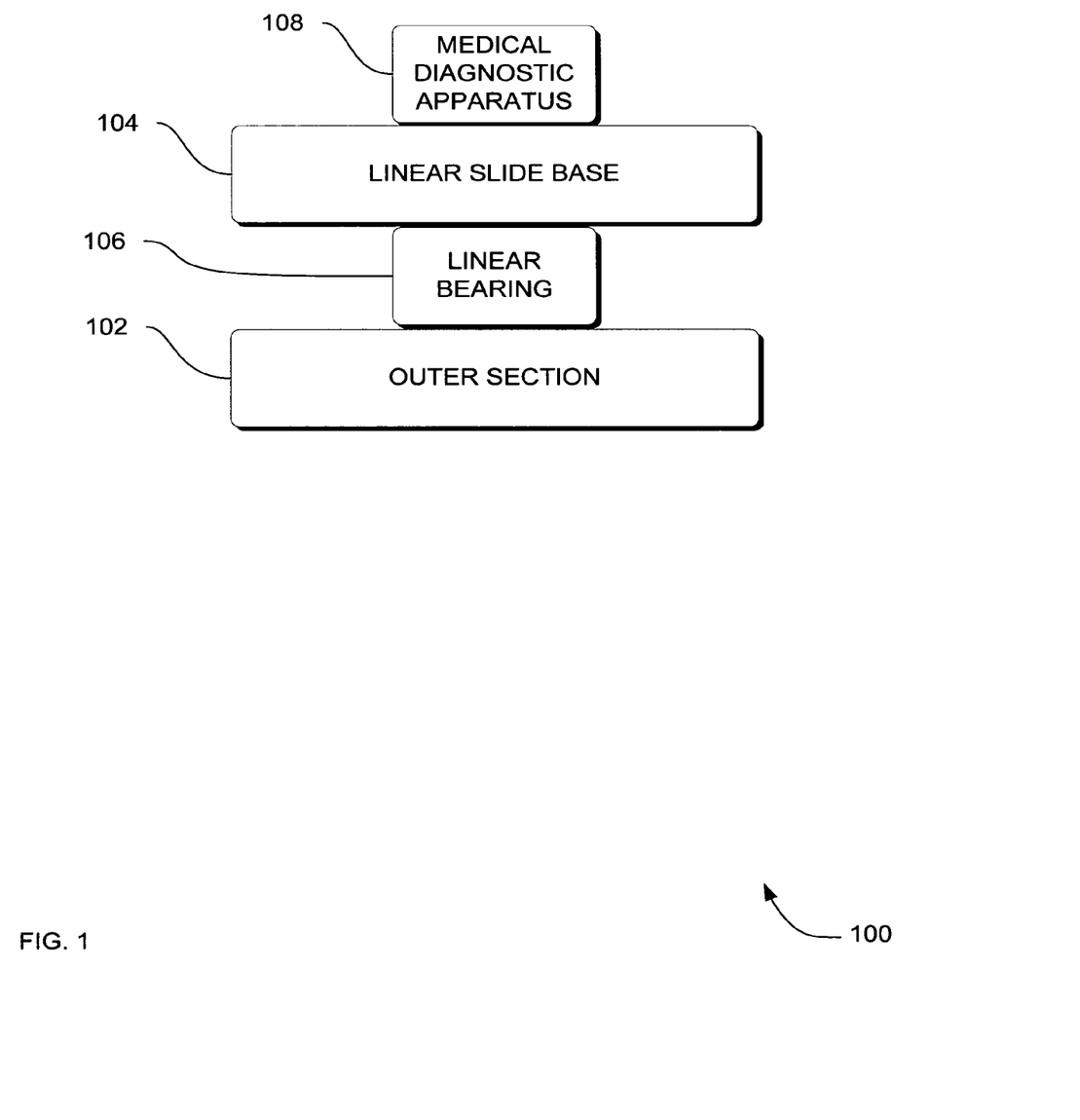
FIG. 1 is a block diagram that provides a system level overview of an asymmetrical extending column that includes linear bearings to provide freedom of motion for general positioning of imaging apparatus at a desired location and orientation.

FIG. 1 is a block diagram that provides a system level overview of an asymmetrical extending column that includes linear bearings to provide freedom of motion for general positioning of imaging apparatus at a desired location and orientation. System 100 solves the need in the art for an extending column that has improved precision of motion, reduced lost motion in the extending column, increased rigidity, as well as reduced size of the extending column.

System 100 includes an outer section 102. The outer section 102 is operably coupled to a first linear slide base 104 through linear bearings 106. In some embodiments, the first linear slide is one of a plurality of linear slide bases. The one or more linear slide bases are constrained to move in a rectilinear motion with respect to each other by linear bearings 106.

In some embodiments one or more medical diagnostic apparatus 108 is mounted on the last of the plurality of linear slide bases. The "last" of the linear slide bases is the linear slide base that is mounted furthest away from the outer section 102. For example, in System 100, the last linear slide base is linear slide base 104.

In some embodiments, the outer section 102 is mountable to a supporting structure (not shown) of the apparatus, such as a ceiling. In those embodiments, the system 100 is suspended from a ceiling over an object that is to be imaged. The supporting structure includes a rotational mount and a carriage attached to the rotational mount. The carriage is mounted or mountable to two stages of overhead ceiling rails. The system 100 allows the medical apparatus 108 to be extended in the direction of the object, and positioned to image the object.

In particular, the linear bearings 106 provide more precise constraint on movement; there is less play and sloppy movement in linear bearings than other forms of moveable attachments. The improved precision of constraint improves rigidity in system 100, which in turn improves precision of motion in system 100. The improved constraint reduces inconsistencies in moving efforts and stiffness, as well as reduces lost motion in the system. Furthermore, the rigidity and improved precision of motion of the linear bearings also improves clinical usage without the need for extensions to achieve a desired anatomical coverage range. In addition, consistency of assembly is also improved because the linear bearings require no adjustments in manufacturing of system 100.

The system level overview of the operation of an embodiment has been described in this section of the detailed description. A system to extend the position of imaging apparatus that implements sections connected by linear bearings has been described. System 100 is described as being asymmetrical because all of the linear motion means are on one side or one plane relative to a center line, the center line being line which pass thru and is surrounded by all the sections. For example, linear slide base 104 extends from outer section 102.

While the system 100 is not limited to any particular outer section 102, linear slide base 104, linear bearings 106 and medical diagnostic apparatus 108, for sake of clarity simplified outer section 102, linear slide base 104, linear bearings 106 and medical diagnostic apparatus 108 has been described.

Figure 2:
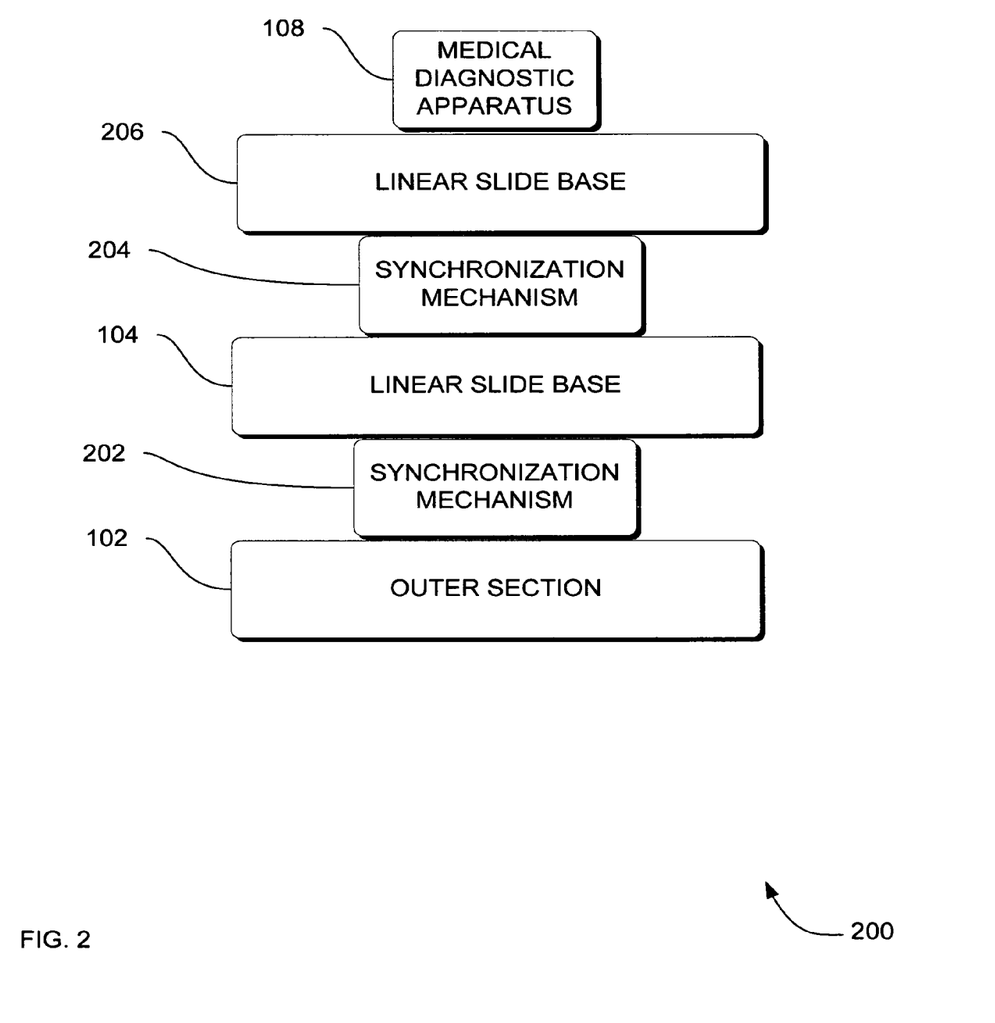
FIG. 2 is a block diagram that provides a system level overview of an asymmetrical extending column that includes a synchronization mechanism to provide freedom of motion for general positioning of imaging apparatus at a desired location and orientation.

FIG. 2 is a block diagram that provides a system level overview of an asymmetrical extending column that includes a synchronization mechanism to provide freedom of motion for general positioning of imaging apparatus at a desired location and orientation. System 200 solves the need in the art to reduce rubbing of J-bars against sections.

System 200 includes an outer section 102. The outer section 102 is operably coupled to a first linear slide base 104 through a synchronization mechanism 202. Furthermore, a second linear slide base 206 is operably coupled to the first linear slide base 104 through a second synchronization mechanism 204. In addition, the first synchronization mechanism 202 is operably coupled to the second synchronization mechanism 204 so that the linear slide bases 104 and 206 each slide in equal distances relative to each other. More specifically, when the first linear slide base 104 moves a distance in a direction relative to outer section 102, the second linear slide base 206 will move the same distance in the same direction relative to the first linear slide base 104. For example, when the first linear slide base 104 moves 1 centimeter forward relative to outer section 102, the second linear slide base 206 will move 1 centimeter forward relative to the first linear slide base 104, and second linear slide base 206 will move 2 centimeters forward relative to the outer section 102.

Synchronization mechanisms 202 and 204 eliminate the rubbing of J-bars against sections because the use of J-bars is eliminated in system 200. The system level overview of the operation of an embodiment has been described in this section of the detailed description. A system to extend the position of imaging apparatus that implements sections connected by synchronization mechanisms has been described.

While the system 200 is not limited to any particular outer section 102, linear slide base 104 and 206, synchronization mechanisms 202 and 204, and medical diagnostic apparatus 108, for sake of clarity simplified outer section 102, linear slide base 104 and 206, synchronization mechanisms 202 and 204 and medical diagnostic apparatus 108 has been described.

Figure 3:
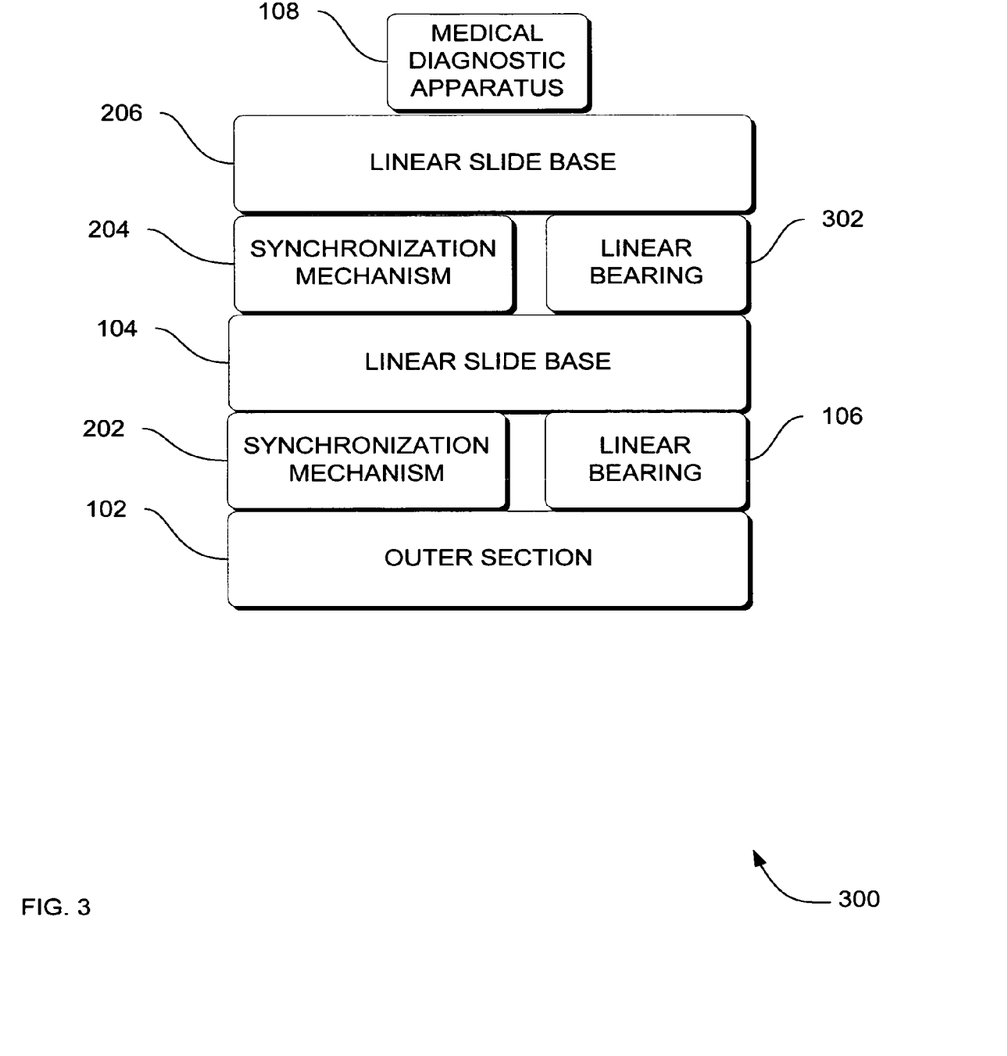
FIG. 3 is a block diagram that provides a system level overview of a three-tiered extending column that includes synchronization mechanisms and linear bearings to provide freedom of motion for general positioning of imaging apparatus at a desired location and orientation.

FIG. 3 is a block diagram that provides a system level overview of a three-tiered extending column that includes synchronization mechanisms and linear bearings to provide freedom of motion for general positioning of imaging apparatus at a desired location and orientation. System 300 combines the components of system 100 and 200, and solves problems that system 100 or system 200 solve.

System 300 includes a liner bearing 302 that operably couples linear slide base 206 and linear slide base 104.

In system 300, rubbing of J-bars against sections is eliminated because J-bars are not implemented in system 300. The linear bearings 106 and 302 provide more precise constraint on movement because linear bearings have less play and sloppy movement than other forms of moveable attachments, which in turn improves rigidity in system 300, which in turn improves precision of motion in system 300. The more precise constraint reduces inconsistencies in moving efforts and stiffness, as well as reduces lost motion in the five-tiered extending column. Furthermore, consistency of assembly is also improved because the linear bearings require no adjustments in manufacturing of system 300.

APPARATUS OF EMBODIMENTS

In the previous section, a system level overview of the operation of an embodiment was described. In this section, the particular apparatus of such an embodiment are described by reference to a series of diagrams.

Figure 4:
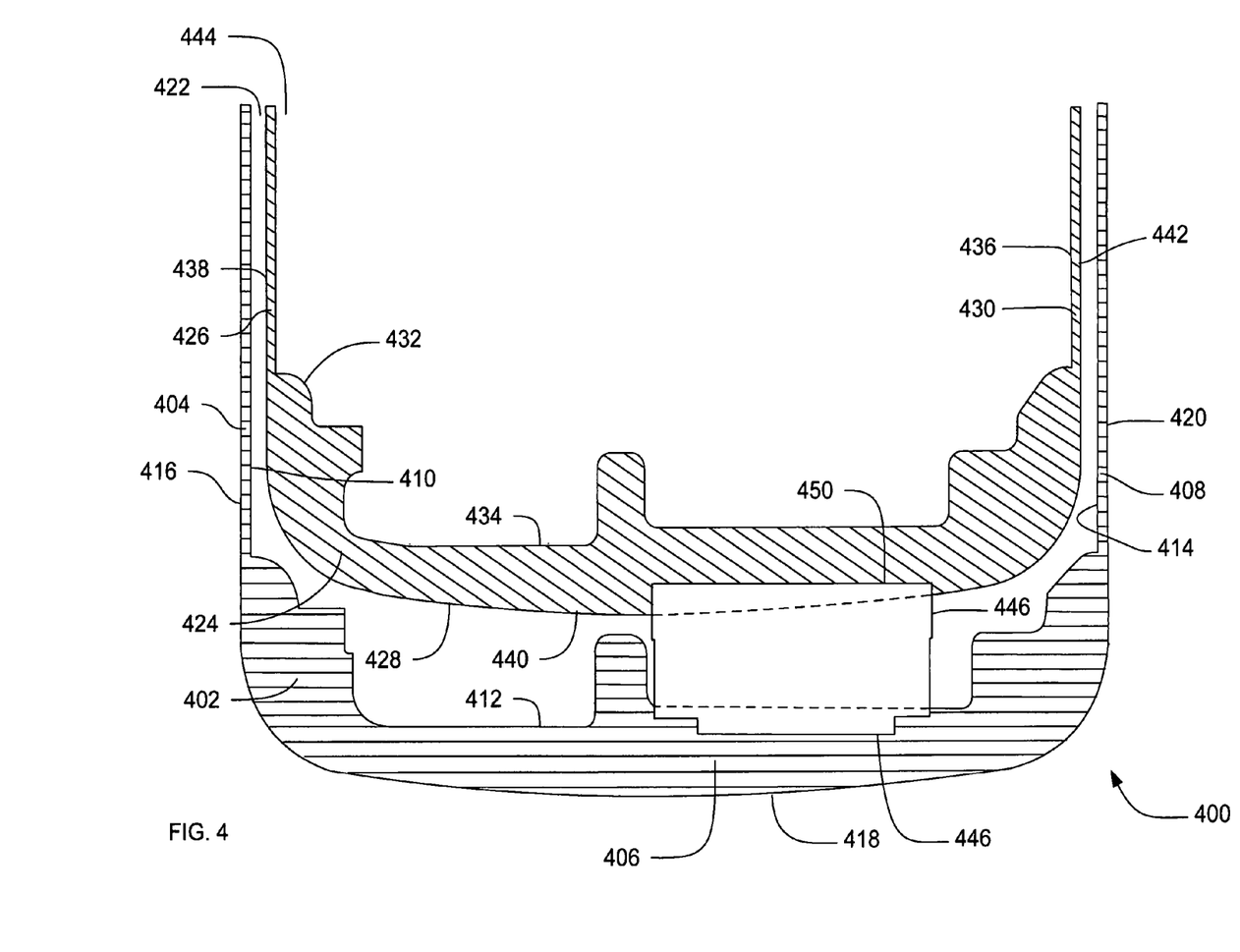
FIG. 4 is an end cross section diagram of apparatus according to an embodiment.

FIG. 4 is an end cross section diagram of apparatus 400 according to an embodiment.

In apparatus 400, the outer section 102 in FIG. 1 is implemented as a first open section 402 of the apparatus 400. The first open section 402 has three sides 404, 406 and 408. Side 406 is the middle side of first open section 402 because side 406 is located between sides 404 and 408. Sides 404, 406 and 408 have inner faces 410, 412, 414 and outer faces 416, 418 and 420, respectively. The first open section also includes a side 422 that is open. The open side 422 lacks closure, thus providing a concave, "U" shape to the first open section 402. The open side 422 is opposite side 406. The first open section 402 also has two ends that are not shown in this cross section diagram 400, each end having an inner face and an outer face. First open section 402 and apparatus 400 also have a longitudinal axis, which is also not shown in FIG. 4. In apparatus 400, the first linear slide base 104 is implemented as a second open section 424. The second open section 424 is similar to the first open section 402 in that the second open section 424 is concave, but with one notable difference: The second open section 424 is smaller than the first open section 402 to the extent that second open section 424 fits into the first open section 402. More specifically, the second open section 424 has outer dimensions that are smaller than the inner dimensions of the first open section 402. The second open section 424 is an embodiment of the linear slide base 104 in FIG. 1.

The second open section 424 has three sides 426, 428 and 430. Side 428 is the middle side of second open section 424 because side 428 is located between sides 426 and 430. Sides 426, 428 and 430 have inner faces 432, 434, 436 and outer faces 438, 440 and 442, respectively. The second open section also includes a side 444 that is open. The open side 444 lacks closure, thus providing a concave, "U" shape to the second open section 424. The open side 444 is opposite side 428. The second open section 424 also has two ends that are not shown in this cross section diagram 400, each end having an inner face and an outer face. Second open section 424 and apparatus 400 also have a longitudinal axis, which is also not shown in FIG. 4. The longitudinal axis of the second open section 424 is aligned in parallel with the longitudinal axis of the first open section 402.

The apparatus 400 also includes a first linear bearing assembly 446. The first linear assembly 446 has a first side 448 and a second side 450. Both sides 448 and 450 are parallel to a motion of the at least one first linear bearing assembly 446. The first side 448 of the first linear bearing assembly 446 is mounted to the first open section 402 on the inner face 412 of the side 406 that is opposite the open side 422 of the first open section 402. The second side 450 of the first linear bearing assembly 446 is mounted to the second open section 424 on the outer face 440 of the side 428 of the second open section 428 that is opposite the open side 444 of the second open section 424.

Implementing one linear bearing assembly in between each section, as in apparatus 400, provides an apparatus that is easier to manufacture than other embodiments of apparatus 400 that include two linear bearing assemblies. Manufacturing the apparatus 400 with one linear bearing assembly 446 easier to manufacture because the one linear bearing assembly 446 does not require adjustments. Manufacturing the apparatus 400 with two or more linear bearing assemblies requires adjustment of the linear bearing assemblies to within about 20 micrometers over a 600 millimeter rail length to provide flatness, parallelism and straightness with sufficient freedom of movement of the sections. Apparatus 400 with two or more linear bearing assemblies is also more torsionally rigid. An apparatus 400 with one linear bearing assembly 446 does have slightly lower torsional rigidity than two linear bearing assemblies, and thus an apparatus 400 with one linear bearing assembly 446 requires a somewhat wider linear bearing assembly 446 than the width of the two linear bearing assemblies in order to provide a higher moment that will be more stable from side-to-side. The support structure of the linear slide base must be sufficiently massive to support the larger torsion moment from the single bearing assembly. Thus, apparatus 400 with two or more linear bearing assemblies is also lighter in weight.

Figure 5:
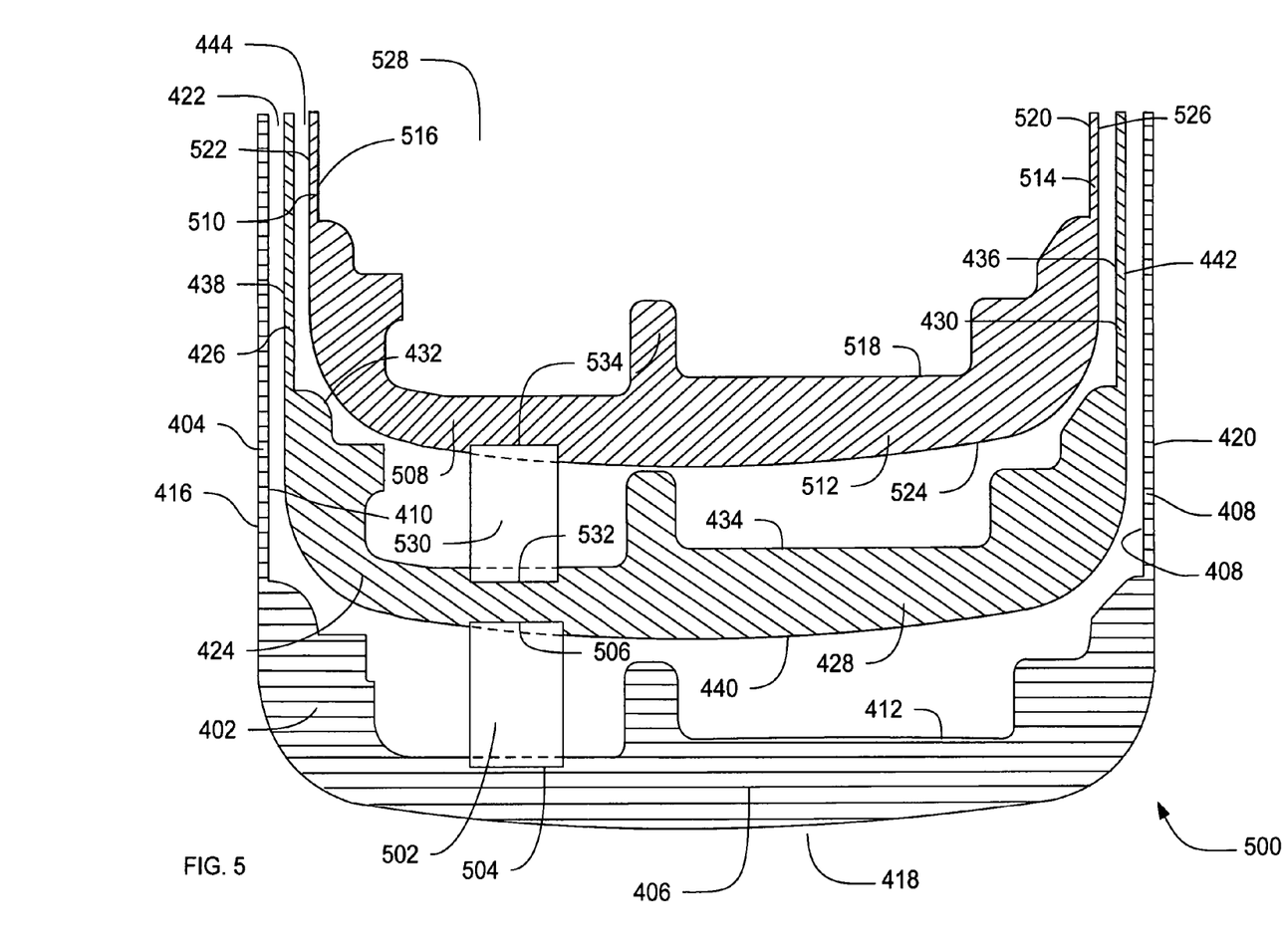
FIG. 5 is an end cross section diagram of apparatus that includes synchronization mechanisms according to an embodiment.

FIG. 5 is an end cross section diagram of apparatus 500 that includes synchronization mechanisms according to an embodiment. The gear, rack, and chain and sprocket synchronization mechanisms of apparatus 500 coordinate the motion of the sections, so that the sections extend in a proportional manner.

Apparatus 500 also includes a first transportation mechanism 502. The first transportation mechanism 502 has a first side 504 and a second side 506. The first side 504 of the first transportation mechanism 502 is mounted to the first open section 402 on the inner face 412 of the side 406 that is opposite the open side 422 of the first open section 402. The second side 506 of the first transportation mechanism 502 is mounted to the second open section 424 on the outer face 440 of the side 428 of the second open section 428 that is opposite the open side 444 of the second open section 424.

A third open section 508 has three sides 510, 512 and 514. Side 512 is the middle side of third open section 508 because side 512 is located between sides 510 and 514. Sides 510, 512 and 514 have inner faces 516, 518, 520 and outer faces 522, 524 and 526, respectively. The second open section also includes a side 528 that is open. The open side 528 lacks closure, thus providing a concave, "U" shape to the second open section 446. The open side 528 is opposite side 512. The third open section 508 also has two ends that are not shown in this cross section diagram 500, each end having an inner face and an outer face. Third open section 508 and apparatus 500 also have a longitudinal axis, which is also not shown in FIG. 5. The longitudinal axis of the third open section 508 is aligned in parallel with the longitudinal axis of the second open section 424.

Apparatus 500 also includes a second transportation mechanism 530. The second transportation mechanism 530 has a first side 532 and a second side 534. The first side 532 of the second transportation mechanism 530 is mounted to the second open section 424 on the inner face 434 of the side 428 that is opposite the open side 444 of the second open section 424. The second side 534 of the second transportation mechanism 530 is mounted to the third open section 508 on the outer face 524 of the side 512 of the third open section 508 that is opposite the open side 528 of the third open section 508.

As the third open section 508 is extended a distance relative to the first open section 402, the second open section 424 extends approximately ½ of the distance. By this means, complete and equal synchronization of the column sections 508, 424 and 402 is accomplished.

Figure 6:
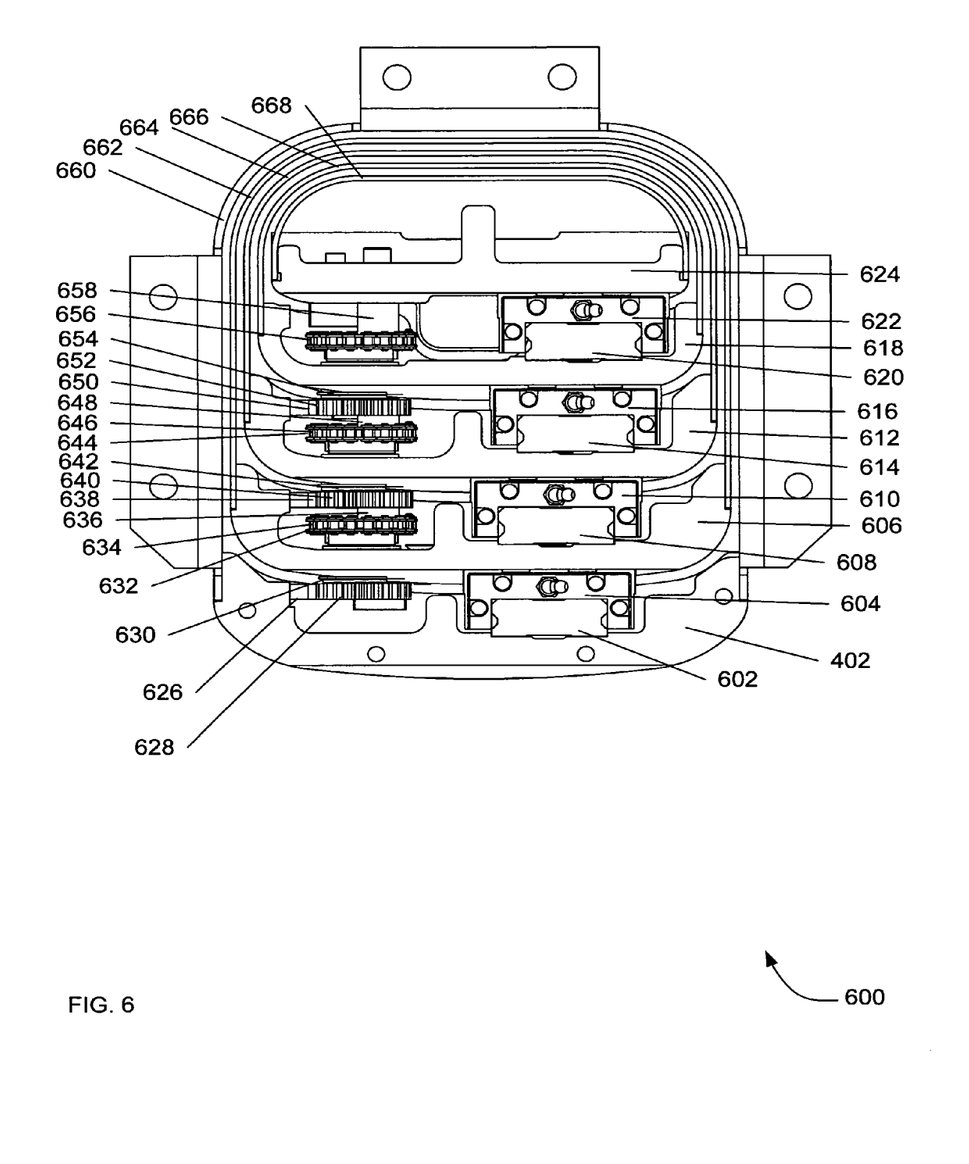
FIG. 6 is a cross section block diagram of a five-tiered extending column with covers on each section that includes gear, rack, and chain and sprocket synchronization mechanisms and linear bearings, according to an embodiment.

FIG. 6 is a cross section block diagram of a five-tiered extending column 600 with covers on each section that includes gear, rack, and chain and sprocket synchronization mechanisms and linear bearings, according to an embodiment. Apparatus 600 solves the need in the art for an extending column that has improved precision of motion, reduced lost motion in the extending column, reduced rubbing of J-bars against sections, increased rigidity, as well as reduced size of the extending column.

Five-tiered extending column 600 also includes a linear bearing assembly 448 that includes a linear bearing rail 602 and one or more linear bearing blocks 604. The linear bearing rail 602 is attached to outer section 102 (e.g. first open section 402). The linear bearing rail 602 is operable to engage with the one or more linear bearing blocks 604.

The first moveable section 606 (e.g. second open section 424) is attached to the one or more linear bearing blocks 604. The first moveable section 606 is attached to a linear bearing rail 608 that is in turn engaged to a linear bearing block 610, that is in turn attached to a second moveable section 612 (e.g. third open section 508).

The second moveable section 612 is attached to a linear bearing rail 614 that is in turn operable to engage a linear bearing block 616, that is in turn attached to a third moveable section 618.

The third moveable section 618 is attached to a linear bearing rail 620 that is in turn engaged to a linear bearing block 622, that is in turn attached to a fourth moveable section 624. In some embodiments, the fourth moveable section 624 is attached to medical diagnostic apparatus 108 (not shown) such as an X-ray source and collimator.

Attached to the first open section 402 is a gear rack 626 that is aligned approximately in parallel to linear bearing rail 602. The gear rack 626 is engaged by a circular gear 628 mounted to a shaft 630. The shaft 630 is rotatably mounted to the first movable section 606.

Attached to the shaft 640 is a sprocket 632 which is selected to have a pitch line diameter approximately equal to the pitch line diameter of the gear rack 626. The sprocket 632 engage a chain 634 which forms a loop about an idler (not shown) wherein at least one side of the chain loop is constrained to move in a direction approximately parallel to linear bearing rail 608. Note that the pitch line diameters can be slightly different, with the effect that the motions of the sections are not in the exact proportions. For small deviations, this is not objectionable.

Attached to the chain 634 is a block 636, which is also attached to the second movable section 612.

When the first movable section 606 is moved, the circular gear 628 rotatably engages the rack 626, imparting rotational motion to the shaft 630 and thus to the sprocket 632. The sprocket 632 drives the chain 634 which drives the block 636, which in turn drives the second movable section 612. With the pitchline diameter of the circular gear 628 approximately equal to the pitchline diameter of the sprocket 632, the motion imparted to the second movable section 612 will be twice that motion which was imparted to the first movable section 402. It should be noted that exact equality of pitchline diameters is not required.

The synchronization apparatus is implemented twice more, with a gear rack 638 mounted to the second movable section 606 engaging a circular gear 640 on a shaft 642 mounted to the second movable section 606, driving a sprocket 644 that in turn drives a chain 646 with a block 648 attached to the third movable section 612, and again with a gear rack 650 mounted to the third movable section 612 engaging a circular gear 652 on a shaft 654 mounted to the third movable section 618, driving a chain 656 with a block 658 attached to the fourth movable section 624.

As the fourth movable section is extended a distance, the third movable section extends approximately ¾ of the distance, the second movable section extends approximately ½ of the distance, and the first movable section extends approximately ¼ of the distance. Thus five-tiered extending column 600 provides complete synchronization of the column sections 402, 606, 612, 618 and 624 is accomplished.

The shafts and gears of five-tiered extending column 600 can be of one piece, or the shaft and sprocket can be of one piece, and other variations can be implemented, such as a block being part of the section, as opposed to being a separate piece without departing from the spirit of the five-tiered extending column 600.

Furthermore, other components which perform the same function(s) as a gear, rack, and chain and sprockets are implemented without departing from the spirit of the five-tiered extending column 600, for example, in some embodiments, the chain and sprockets replaced by a timing belt and timing belt sprockets, the gear and rack are replaced by a stationary chain with an ascending sprocket, etc.

Sections 402, 606, 612, 618 and 624 have sufficient stiffness to provide torsional and bending rigidity for the five-tiered extending column 600. In some embodiments, in which the sections 402, 606, 612, 618 and 624 are made from aluminum, the weight of the first open section 402 is at least 3.8 and not more than 15.2 pounds per lineal foot of extrusion. In the aluminum embodiment, fifth open section 624 has weight of at least 2.35 and not more than 9.4 pounds per lineal foot of extrusion. For intermediate sections 606, 612 and 618, the weight is between a lower and upper limit, in proportion to the section location, according to the Formula 1 below:

$$Wn=W1+(n-1)/(N-1)*(WN-W1) \quad \text{Formula 1}$$

In formula, n represents a section number counting from the innermost section, the fifth open section 624 and towards the outermost section, the first open section 402, with the innermost section being equal to n=1. Furthermore, W represents a weight per foot of the section n. In addition, W1 represents a weight per foot of the innermost section, the fifth open section 624. In Formula 1, N represents account of the sections, which five in the five-tiered extending column 600. WN represents a weight per foot of the outermost section, the first open section 402.

Applying Formula 1 to determine the lower limit of the weight per lineal foot of extrusion measured in pounds for the fifth open section 624 is shown in Formula 2 below:

$$W_2=(2.35)+(1)/(4)*(3.8-2.35)=2.71 \text{ lbs/foot} \quad \text{Formula 2}$$

In Formula 2, where the weight per foot of the innermost section, the fifth open section 624, W1 is 2.35 lbs; and the weight per foot of the outermost section, the first open section 402, WN is 3.8 lbs, the calculation indicates that the lower limit of the fourth open section 618 is 2.71 lbs/foot.

Applying Formula 1 to determine the upper limit of the weight per lineal foot of extrusion measured in pounds for the fourth open section 618 is shown in Formula 3 below:

$$W_2=(9.4)+(1)/(4)*(15.2-9.4)=10.85 \text{ lbs/foot} \quad \text{Formula 3}$$

In Formula 3, where the weight per foot of the innermost section, the fifth open section 624, W1 is 9.4 lbs; and the weight per foot of the outermost section, the first open section 402, WN is 15.2 lbs, the calculation indicates that the lower limit of the fourth open section 618 is 10.85 lbs/foot.

Applying Formula 1 to determine the lower limit of the weight per lineal foot of extrusion measured in pounds for the third open section 612 is shown in Formula 4 below:

$$W_3=(2.35)+(2)/(4)*(3.8-2.35)=3.07 \text{ lbs/foot} \quad \text{Formula 4}$$

In Formula 4, where the weight per foot of the innermost section, the fifth open section 624, W1 is 2.35 lbs; and the weight per foot of the outermost section, the first open section 402, WN is 3.8 lbs, the calculation indicates that the lower limit of the third open section 612 is 2.71 lbs/foot.

Applying Formula 1 to determine the upper limit of the weight per lineal foot of extrusion measured in pounds for the third open section 612 is shown in Formula 5 below:

$$W_3=(9.4)+(2)/(4)*(15.2-9.4)=12.3 \text{ lbs/foot} \quad \text{Formula 5}$$

In Formula 5, where the weight per foot of the innermost section, the fifth open section 624, W1 is 9.4 lbs; and the weight per foot of the outermost section, the first open section 402, WN is 15.2 lbs, the calculation indicates that the upper limit of the third open section 618 is 12.3 lbs/foot.

Applying Formula 1 to determine the lower limit of the weight per lineal foot of extrusion measured in pounds for the second open section 608 is shown in Formula 6 below:

$$W_4=(2.35)+(3)/(4)*(3.8-2.35)=3.44 \text{ lbs/foot} \quad \text{Formula 6}$$

In Formula 6, where the weight per foot of the innermost section, the fifth open section 624, W1 is 2.35 lbs; and the weight per foot of the outermost section, the first open section 402, WN is 3.8 lbs, the calculation indicates that the lower limit of the second open section 608 is 3.44 lbs/foot.

Applying Formula 1 to determine the upper limit of the weight per lineal foot of extrusion measured in pounds for the second open section 608 is shown in Formula 7 below:

$$W_4=(9.4)+(3)/(4)*(15.2-9.4)=13.7 \text{ lbs/foot} \quad \text{Formula 7}$$

In Formula 7, where the weight per foot of the innermost section, the fifth open section 624, W1 is 9.4 lbs; and the weight per foot of the outermost section, the second open section 608, WN is 15.2 lbs, the calculation indicates that the upper limit of the second open section 608 is 13.7 lbs/foot.

These lower and upper weights per foot for the sections refer to the average weight, which is the weight of the section, divided by the length of the section.

Formula 1 is applicable to five-tiered extending column 600 as shown above, and to intermediate sections of a similar column design having a number of sections that is greater or less than five.

In some embodiments, the sections are enclosed by covers. For example, the outer section 102 is attached to a cover 660, the second open section 606 is attached to a cover 662, the third open section 612 is attached to a cover 664, the fourth open section 618 is attached to a cover 666, and the fifth open section 624 is attached to a cover 668. The covers improve stiffness of the five-tiered extending column 600 and protect the components and improves the aesthetics of the five-tiered extending column 600.

The linear bearings 106 provide more precise constraint on movement because linear bearings have less play and sloppy movement than other forms of moveable attachments. The improved precision of constraint improves rigidity in five-tiered extending column 600, which in turn improves precision of motion in five-tiered extending column 600. The improved constraint reduces inconsistencies in moving efforts and stiffness, as well as reduces lost motion in the five-tiered extending column. The rubbing of J-bars against sections is also eliminated because the use of J-bars is eliminated in five-tiered extending column 600. Furthermore, the rigidity and improved precision of motion of the linear bearings also improves clinical usage without the need for extensions to achieve a desired anatomical coverage range. In addition, consistency of assembly is also improved because the linear bearings require no adjustments in manufacturing of five-tiered extending column 600. Yet, the five-tiered extending column 600 also displaces a relatively small volume.

Figure 7:
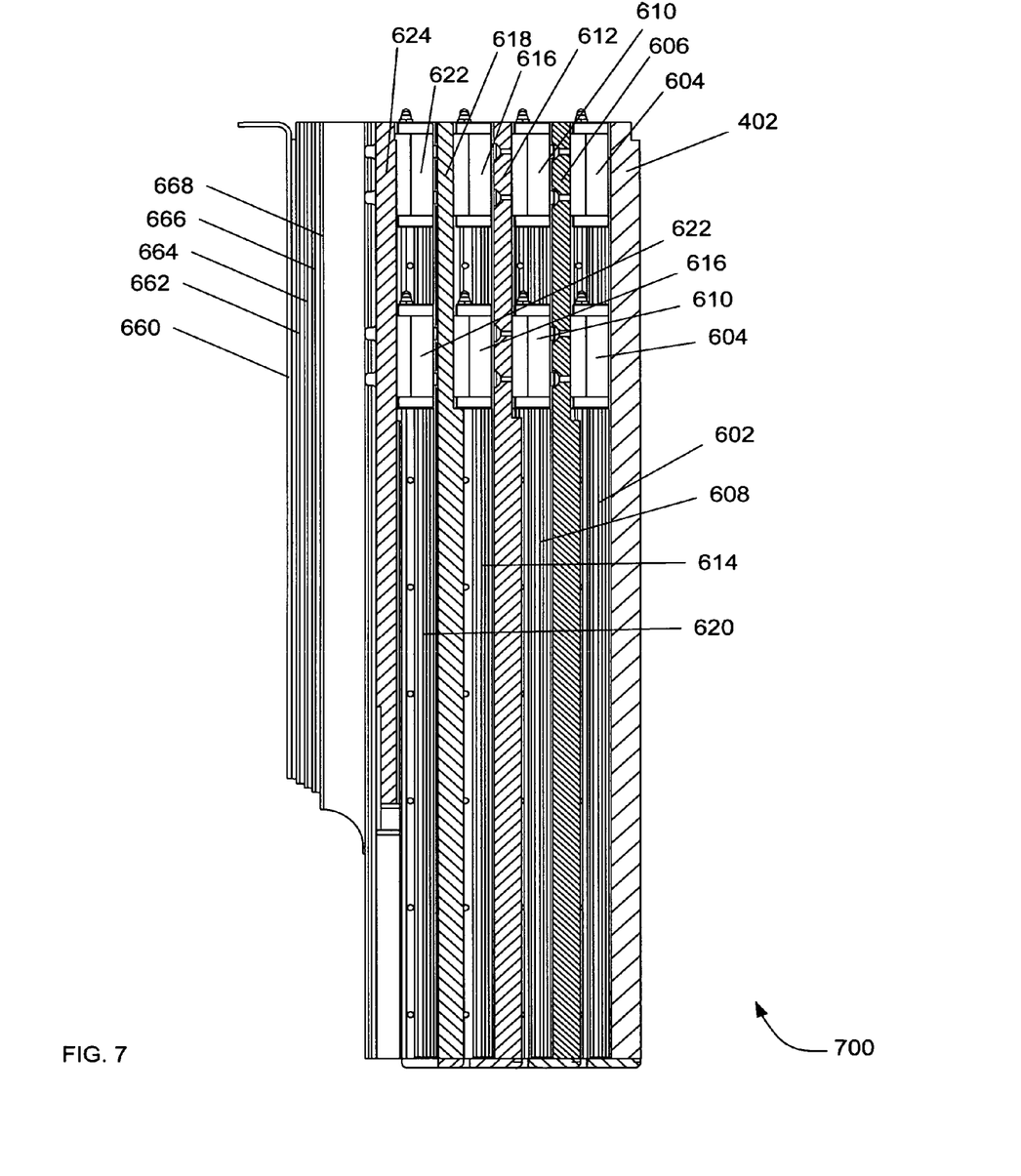
FIG. 7 is a longitudinal cross section block diagram of a five-tiered extending column in a retracted position with covers on each section that includes gear, rack, chain and sprocket synchronization mechanisms and linear bearings, according to an embodiment.

FIG. 7 is a longitudinal cross section block diagram of a five-tiered extending column 700 in a retracted position with covers on each section that includes gear, rack, chain and sprocket synchronization mechanisms and linear bearings, according to an embodiment.

Figure 8:
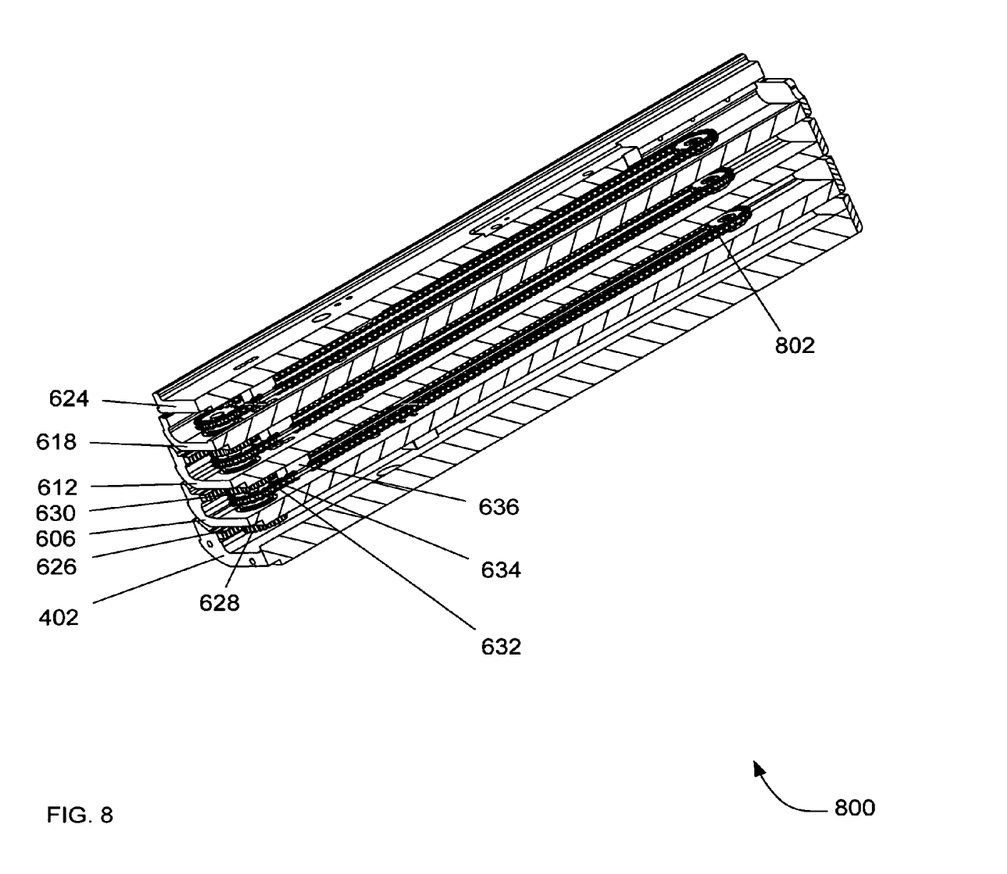
FIG. 8 is an azimuthal cross section block diagram of a five-tiered extending column 800 in a fully retracted position without covers showing gear, rack, chain and sprocket synchronization mechanisms, according to an embodiment.

FIG. 8 is an azimuthal cross section block diagram of a five-tiered extending column 800 in a fully retracted position without covers showing gear, rack, chain and sprocket synchronization mechanisms, according to an embodiment. The five-tiered extending column 800 includes a chain idler 802.

Figure 9:
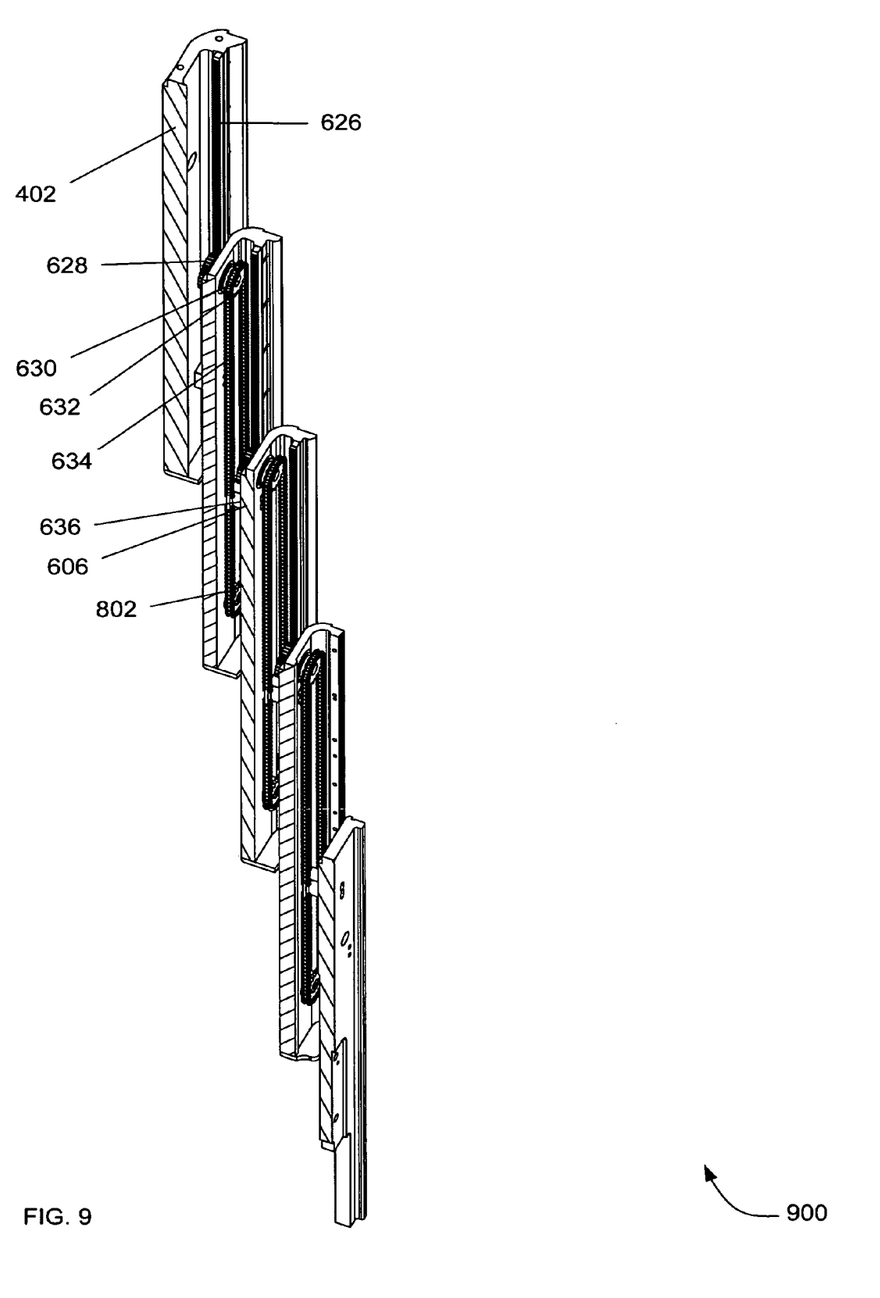
FIG. 9 is an azimuthal cross section block diagram of a five-tiered extending column in an extended position without covers showing gear, rack, chain and sprocket synchronization mechanisms, according to an embodiment.

FIG. 9 is an azimuthal cross section block diagram of a five-tiered extending column 900 in an extended position without covers showing gear, rack, chain and sprocket synchronization mechanisms, according to an embodiment.

Figure 10:
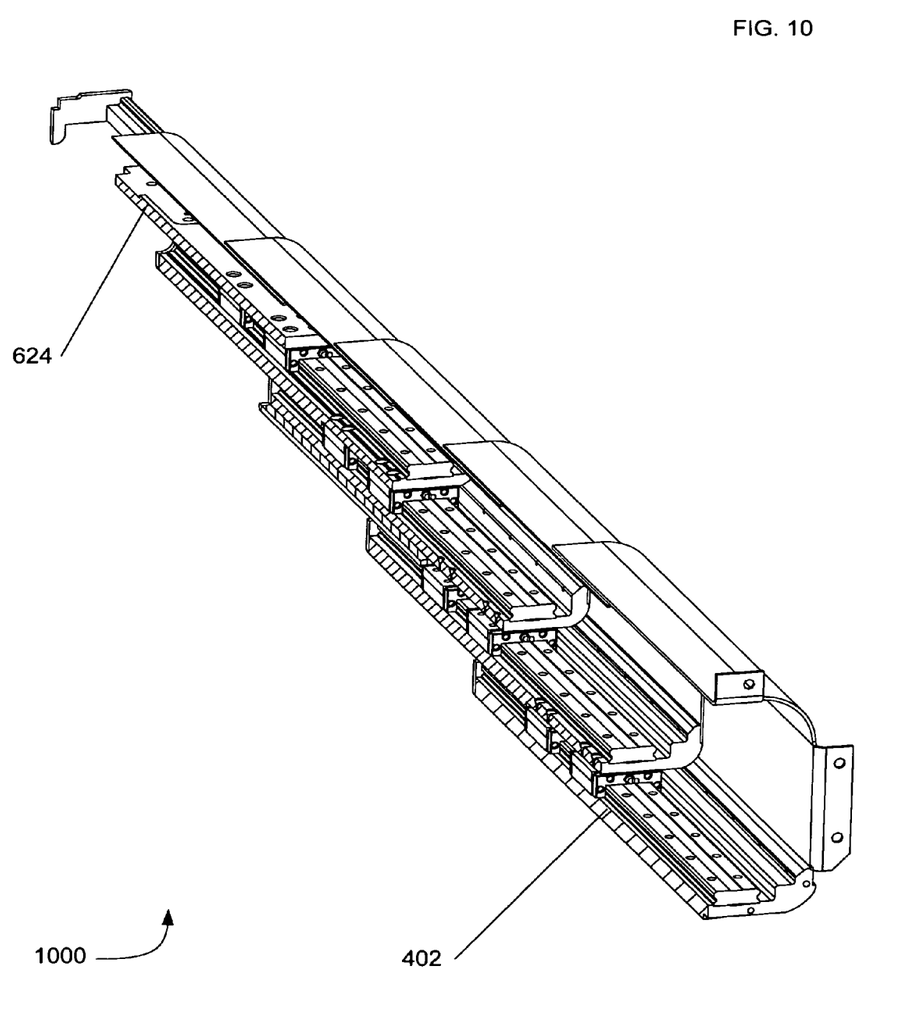
FIG. 10 is a cross section block diagram of a five-tiered extending column in a partly extended position without covers showing gear, rack, chain and sprocket synchronization mechanisms, according to an embodiment.

FIG. 10 is a cross section block diagram of a five-tiered extending column 1000 in a partly extended position without covers showing gear, rack, chain and sprocket synchronization mechanisms, according to an embodiment. The first open section 402 is positioned closest in perspective, while the fifth open section 624 is extended away from the first open section and is furthest away in perspective.

Figure 11:
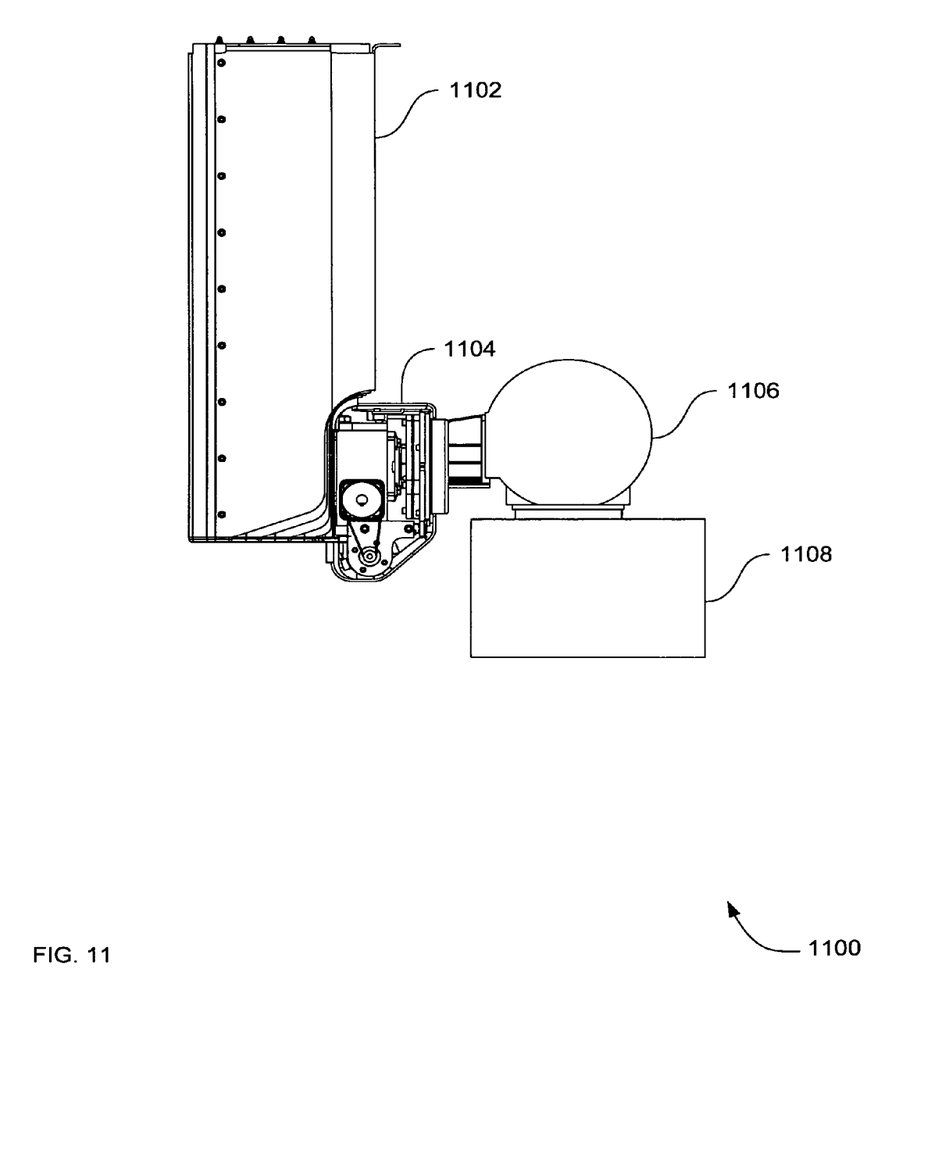
FIG. 11 is a side view of fifth open section of an extending column with a drive, and X-ray source and a collimator mounted to the last open section, according to an embodiment.

FIG. 11 is a side view of fifth open section of five-tiered extending column in an extended position with a drive, and X-ray source and a collimator mounted to the fifth open section, according to an embodiment.

Apparatus 1100 includes an extending column 1102. The extending column 1102 may be embodied as any one of the embodiments describe by systems 100, 200 and 300; apparatus 400 and 500, extending columns 600, 700, 800, 900 and 1000.

A drive 1104 is mounted to the extending column 1102, such as an electric drive, that positions an X-ray source 1106 and a collimator in one or more axis of movement, relative to the extending column 1100. Apparatus 1100 provides a mechanized means of positioning the X-Ray source 1106 and the collimator 1108 that is faster and more precise than manual means of positioning the equipment.

CONCLUSION

An extending column has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future medical diagnostic equipment, different materials, and new sprockets, gears, shafts, chains and bearings.

The terminology used in this application with respect to linear bearing assemblies and synchronization mechanisms is meant to include all linear bearing assemblies and synchronization mechanisms and alternate technologies which provide the same functionality as described herein.

We claim:

1. An apparatus comprising:
   an outer section, mountable to a supporting structure for the apparatus;
   a plurality of moveable sections, a first moveable section of the plurality of moveable sections being mounted on the outer section, the plurality of moveable sections being constrained to move in a rectilinear motion with respect to each other by linear bearings, wherein the plurality of moveable sections further comprises at least three moveable sections, wherein each of the moveable sections have an outer dimension of cross sectional size that are successively nested; and
   at least one medical diagnostic apparatus mounted on the last of the plurality of moveable sections.

2. The apparatus of claim 1, wherein the plurality of moveable sections further comprises four moveable sections.

3. The apparatus of claim 1, wherein the outer section further comprises:
   a first open section, having two ends, three sides, an open side, the open side being opposite one of the three sides, each of the ends and sides having an inner face and an outer face, and a longitudinal axis;
   wherein the plurality of moveable sections further comprise:
   a second open section, having two ends, three sides, an open side, the open side being opposite one of the three sides, each of the ends and sides having an inner face and an outer face, and a longitudinal axis, the second open section having an outer dimension of a cross sectional size that is smaller than an inner dimension of the cross section size of the first open section, the longitudinal axis of the second open section being aligned in parallel with the longitudinal axis of the first open section; and
   at least one first linear bearing assembly, having a first side and a second side, both sides being parallel to a motion of the at least one first linear bearing assembly, the first side of the at least one first linear bearing assembly being mounted to the first open section on the inner face of the side of the first open section side that is opposite the open side of the first open section, the second side of the at least one first linear bearing assembly being mounted to the second open section on the outer face of the side of the second open section side that is opposite the open side of the second open section.

4. The apparatus of claim 3, wherein each of the open sides and the outer section are enclosed by covers.

5. The apparatus of claim 3, wherein the first open section and the second open section move in a rectilinear motion with respect to each other on the at least one first linear bearing assembly.

6. The apparatus of claim 3, wherein the at least one first linear bearing assembly further comprises one linear bearing assembly.

7. The apparatus of claim 3, wherein the at least one first linear bearing assembly further comprises:
   a linear bearing rail; and
   at least one linear bearing block, the at least one linear bearing block being engaged with the linear bearing rail.

8. The apparatus of claim 7, wherein the linear bearing rail further comprises the first side of the at least one first linear bearing assembly and wherein the at least one linear bearing block further comprises the second side of the at least one first linear bearing assembly.

9. The apparatus of claim 7, wherein the linear bearing rail further comprises a linear bearing rail mounted to the inner face of the side of the first open section side that is opposite the open side of the first open section, and wherein the linear bearing block further comprises a linear bearing block mounted to the outer face of the side of the second open section side that is opposite the open side of the second open section.

10. The apparatus of claim 7, wherein the at least one linear bearing block further comprises two linear bearing blocks.

11. The apparatus of claim 3, wherein the three sides and the open side of each open section further comprises a u-shaped section in cross section.

12. The apparatus of claim 3, wherein each open section further comprises u-shaped in cross section.

13. The apparatus of claim 3, the plurality of moveable sections further comprising:
   a third open section, having two ends, three sides, an open side, the open side being opposite one of the three sides, each of the ends and sides having an inner face and an outer face, and a longitudinal axis, the third open section having an outer dimension of a cross sectional size that is smaller than an inner dimension of the cross section size of the second open section, the longitudinal axis of the third open section being aligned in parallel with the longitudinal axis of the second open section;

at least one second linear bearing assembly, having a first side and a second side, both sides being parallel to a motion of the at least one second linear bearing assembly, the first side of the at least one second linear bearing assembly being mounted to the second open section on the inner face of the side of the second open section side that is opposite the open side of the second open section, the second side of the at least one first linear bearing assembly being mounted to the third open section on the outer face of third side the third open section side that is opposite the open side of the second open section;

a fourth open section, having two ends, three sides, an open side, the open side being opposite one of the three sides, each of the ends and sides having an inner face and an outer face, and a longitudinal axis, the fourth open section having an outer dimension of a cross sectional size that is smaller than an inner dimension of the cross section size of the third open section, the longitudinal axis of the fourth open section being aligned in parallel with the longitudinal axis of the third open section;

at least one third linear bearing assembly, having a first side and a second side, both sides being parallel to a motion of the at least one third linear bearing assembly, the first side of the at least one third linear bearing assembly being mounted to the third open section on the inner face of the side of the third open section side that is opposite the open side of the third open section, the second side of the at least one first linear bearing assembly being mounted to the fourth open section on the outer face of fourth side the fourth open section side that is opposite the open side of the third open section;

a fifth open section, having two ends, three sides, an open side, the open side being opposite one of the three sides, each of the ends and sides having an inner face and an outer face, the fifth open section having a longitudinal axis, the fifth open section having an outer dimension of a cross sectional size that is smaller than an inner dimension of the cross section size of the fourth open section, the longitudinal axis of the fifth open section being aligned in parallel with the longitudinal axis of the fourth open section; and at least one fourth linear bearing assembly, having a first side and a second side, both sides being parallel to a motion of the at least one fourth linear bearing assembly, the first side of the at least one fourth linear bearing assembly being mounted to the fourth open section on the inner face of the side of the fourth open section side that is opposite the open side of the fourth open section, the second side of the at least one first linear bearing assembly being mounted to the fifth open section on the outer face of fifth side the fifth open section side that is opposite the open side of the fourth open section.

14. The apparatus of claim 13, wherein each of the open sections move in a rectilinear motion with respect to each other on the linear bearing assemblies,
    wherein each of the at least one linear bearing assemblies further comprises one linear bearing assembly,
    wherein each of the one linear bearing assemblies further comprises:
        a linear bearing rail; and
        a linear bearing block, the linear bearing block being engaged with the linear bearing rail,
    wherein each of the linear bearing rails further comprises:
        a linear bearing rail mounted to the inner face of the side of the associated open section side that is opposite the open side of the associated open section, and
    wherein each of the linear bearing blocks further comprises:
        a linear bearing block mounted to the outer face of the side of the associated open section side that is opposite the open side of the associated open section, and
    wherein each open section further comprises a u-shape in cross section.

15. The apparatus of claim 13, wherein the three sides and the open side of each open section further comprises a u-shaped section in cross section.

16. The apparatus of claim 1, wherein the supporting structure further comprises:
    a rotational mount; and
    a carriage attached to the rotational mount, the carriage being mountable to two stages of overhead ceiling rails.

17. A system comprising:
    an outer section, mountable to a supporting structure for the system; and
    a plurality of concave moveable sections, a first moveable section of the plurality of moveable sections being mounted on the outer section, each concave moveable section being successively smaller than an immediately previous concave moveable section to the extent that each concave moveable section fits into the immediately previous concave moveable section, the plurality of moveable sections being constrained to move in a rectilinear motion with respect to each other by linear bearings, wherein the plurality of concave moveable sections further comprises at least three concave moveable sections.

18. The system of claim 17, wherein the plurality of concave moveable sections further comprises five moveable sections.

19. The system of claim 17, wherein the outer section further comprises:
    a first open section, having two ends, three sides, an open side, the open side being opposite one of the three sides, each of the ends and sides having an inner face and an outer face, and a longitudinal axis;
    wherein the plurality of concave moveable sections further comprises:
        a second open section, having two ends, three sides, an open side, the open side being opposite one of the three sides, each of the ends and sides having an inner face and an outer face, and a longitudinal axis, the second open section having an outer dimension of a cross sectional size that is smaller than an inner dimension of the cross section size of the first open section, the longitudinal axis of the second open section being aligned in parallel with the longitudinal axis of the first open section; and
        at least one first linear bearing assembly, having a first side and a second side, both sides being parallel to a motion of the at least one first linear bearing assembly, the first side of the at least one first linear bearing assembly being mounted to the first open section on the inner face of the side of the first open section side that is opposite the open side of the first open section, the second side of the at least one first linear bearing assembly being mounted to the second open section on the outer face of the side of the second open section side that is opposite the open side of the second open section.

20. The system of claim 19, wherein the first open section and the second open section move in a rectilinear motion with respect to each other on the at least one first linear bearing assembly.

21. The system of claim 19, wherein the at least one first linear bearing assembly further comprises one linear bearing assembly.

22. The system of claim 19, wherein the at least one first linear bearing assembly further comprises:
   a linear bearing rail; and
   two linear bearing blocks, the linear bearing blocks being engaged with the linear bearing rail.

23. The system of claim 22, wherein the linear bearing rail further comprises the first side of the at least one first linear bearing assembly and wherein the two linear bearing blocks further comprises the second side of the at least one first linear bearing assembly.

24. The system of claim 22, wherein the linear bearing rail further comprises a linear bearing rail mounted to the inner face of the side of the first open section side that is opposite the open side of the first open section, and wherein the two linear bearing blocks further comprise two linear bearing blocks each of which are mounted to the outer face of the side of the second open section side that is opposite the open side of the second open section.

25. The system of claim 19, wherein the three sides and the open side of each open section further comprises a u-shaped section in cross section.

26. The system of claim 19, wherein each open section further comprises u-shaped in cross section.

27. The system of claim 19, the plurality of concave moveable sections further comprises:
   a third open section, having two ends, three sides, an open side, the open side being opposite one of the three sides, each of the ends and sides having an inner face and an outer face, and a longitudinal axis, the third open section having an outer dimension of a cross sectional size that is smaller than an inner dimension of the cross section size of the second open section, the longitudinal axis of the third open section being aligned in parallel with the longitudinal axis of the second open section;
   at least one second linear bearing assembly, having a first side and a second side, both sides being parallel to a motion of the at least one second linear bearing assembly, the first side of the at least one second linear bearing assembly being mounted to the second open section on the inner face of the side of the second open section side that is opposite the open side of the second open section, the second side of the at least one first linear bearing assembly being mounted to the third open section on the outer face of third side the third open section side that is opposite the open side of the second open section;
   a fourth open section, having two ends, three sides, an open side, the open side being opposite one of the three sides, each of the ends and sides having an inner face and an outer face, and a longitudinal axis, the fourth open section having an outer dimension of a cross sectional size that is smaller than an inner dimension of the cross section size of the third open section, the longitudinal axis of the fourth open section being aligned in parallel with the longitudinal axis of the third open section;
   at least one third linear bearing assembly, having a first side and a second side, both sides being parallel to a motion of the at least one third linear bearing assembly, the first side of the at least one third linear bearing assembly being mounted to the third open section on the inner face of the side of the third open section side that is opposite the open side of the third open section, the second side of the at least one first linear bearing assembly being mounted to the fourth open section on the outer face of fourth side the fourth open section side that is opposite the open side of the third open section;
   a fifth open section, having two ends, three sides, an open side, the open side being opposite one of the three sides, each of the ends and sides having an inner face and an outer face, the fifth open section having a longitudinal axis, the fifth open section having an outer dimension of a cross sectional size that is smaller than an inner dimension of the cross section size of the fourth open section, the longitudinal axis of the fifth open section being aligned in parallel with the longitudinal axis of the fourth open section; and
   at least one fourth linear bearing assembly, having a first side and a second side, both sides being parallel to a motion of the at least one fourth linear bearing assembly, the first side of the at least one fourth linear bearing assembly being mounted to the fourth open section on the inner face of the side of the fourth open section side that is opposite the open side of the fourth open section, the second side of the at least one first linear bearing assembly being mounted to the fifth open section on the outer face of fifth side the fifth open section side that is opposite the open side of the fourth open section.

28. The system of claim 19, wherein each of the open sections move in a rectilinear motion with respect to each other on the linear bearing assemblies,
   wherein each of the at least one linear bearing assemblies further comprises one linear bearing assembly,
   wherein each of the one linear bearing assemblies further comprises:
      a linear bearing rail; and
      two linear bearing blocks, the two linear bearing blocks being engaged with the linear bearing rail,
   wherein each of the linear bearing rails further comprises:
      a linear bearing rail mounted to the inner face of the side of the associated open section side that is opposite the open side of the associated open section, and
   wherein each of the two linear bearing blocks further comprises:
      a linear bearing block mounted to the outer face of the side of the associated open section side that is opposite the open side of the associated open section, and
   wherein each open section further comprises a u-shape in cross section.

29. The system of claim 19, wherein the three sides and the open side of each open section further comprises a u-shaped section in cross section.

30. The system of claim 17, wherein the supporting structure further comprises:
   a rotational mount; and
   a carriage attached to the rotational mount, the carriage being mountable to two stages of overhead ceiling rails.

\* \* \* \* \*